US007364758B2

(12) United States Patent
Hsu (10) Patent No.: US 7,364,758 B2
(45) Date of Patent: Apr. 29, 2008

(54) PHARMACEUTICAL USE OF GRAPTOPETALUM AND RELATED PLANTS

(76) Inventor: Shih-Lan Hsu, #3, 8F-5, Sec. 3, Sin-Hai Road Da-an District, Taipei 106 (TW)

( * ) Notice: Subject to any disclaimer, the term of this patent is extended or adjusted under 35 U.S.C. 154(b) by 58 days.

(21) Appl. No.: 10/931,791

(22) Filed: Aug. 31, 2004

(65) Prior Publication Data

US 2006/0045925 A1  Mar. 2, 2006

(51) Int. Cl.
*A01N 65/00* (2006.01)
*A61K 36/00* (2006.01)
(52) U.S. Cl. ................. 424/725; 424/769; 514/838; 514/893; 514/894
(58) Field of Classification Search ............. 424/725; 514/893, 894, 838
See application file for complete search history.

(56) References Cited

U.S. PATENT DOCUMENTS

| 4,996,200 | A | * | 2/1991 | Nishimura et al. |
| 5,023,252 | A | | 6/1991 | Hseih |
| 5,911,993 | A | | 6/1999 | Jian et al. |
| 2004/0023909 | A1 | * | 2/2004 | Roy-Chowdhury et al. |

FOREIGN PATENT DOCUMENTS

| CN | 1355254 A | * | 6/2002 |
| JP | 04208223 A | * | 7/1992 |
| JP | 2004026768 A | * | 1/2004 |
| WO | WO 02/05830 A2 | | 1/2002 |

OTHER PUBLICATIONS

Foroncewicz, K. M. et al. Transplantion Proceedings (2003), 35(6): 2310-2312. Anti-CD25 and tacrolimus therapy may not prevent early primary biliary cirrhosis recurrence after liver transplantation: Two case reports.*
Bach, N. et al. The Mount Sinai Journal of Medicine (Sep. 2003), 70(4): 242-250. Primary biliary cirrhosis: A Mount Sinai perspective.*
PTO 06-4732, Translation of Chinese Patent CN 1355254 A: "Echevaria Glauca Polysaccharides [Shilianhua Duotang]" by Ding Qing. Translated by: Schreiber Translations, Inc. (Jun. 2006).*
Worman, H. J. Cirrhosis: What is Cirrhosis?. http://cpmcnet.columbia.edu/dept/gi/cirrhosis.html downloaded May 16, 2006.*
U1, Wayback Machine: http://web.archive.org/web/*/http://cpmcnet.columbia.edu/dept/gi/cirrhosis.html downloaded Aug. 6, 2006.*
Desmet, V.J., et al. (1994). Classification of chronic hepatitis: diagnosis, grading and staging. *Hepatology* 19(6):1513-1520.
Friedman, S.L. (1993). The cellular basis of hepatic fibrosis. Mechanism and treatment strategies. *N Engl J Med*. 328(25):1828-1835.
Giladi, H., et al. (2003). Small interfering RNA inhibits hepatitis B virus replication in mice. *Mol Ther*. 8(5):769-776.
Pines, M., et al. (1997). Halofuginone, a specific inhibitor of collagen type I synthesis, prevents dimethylnitrosamine-induced liver cirrhosis. *J Hepatol*. 27(2):391-398.

Saller, R., et al. (2001). The use of silymarin in the treatment of liver diseases. *Drugs*. 61(14):2035-2063.
Arai, T., et al. (2001). Effect of herb supplement on hepatic enzyme activities in ddY mice. Lab Anim. 35(3):288-291.
Chou, S.T., et al. Antimutagenic potential of *Graptopetalum paraguayense* E. Walther. 2004 Institute of Food Technologists Annual Meeting. Jul. 12-16, 2004, Session 114F, abstract 4, [retrieved Dec. 6, 2005]. Retrieved from the Internet: URL:http://ift.confex.com/ift/techprogram/paper_22911.htm, whole document.
Chung, Y.C., et al. (2005). Studies on the antioxidative activity of *Graptopetalum paraguayense* E. Walther. Food Chemistry 91:419-424.
Hsieh, C.L., et al. (2005). Inhibitory effect of some selected nutraceutic herbs on LDL glycation induced by glucose and glyoxal. J Ethnopharmacol. 102(3):357-363.
Huang, K., et al. (2005). Studies on the inhibitory effect of *Graptopetalum paraguayense* E. Walther extracts on mushroom tyrosinase. Food Chemistry 89:583-587.
Kang, T.H., et al. (2000). Antiproliferative effects of alkaloids from *Sedum sarmentosum* on murine and human hepatoma cell lines. J Ethnopharmacol. 70(2):177-182.
Wu, X.L., et al. (2003). Effect of compound rhodiola sachalinensis A Bor on $CCl_4$-induced liver fibrosis in rats and its probable molecular mechanisms. World J Gastroenterol. 9(7):1559-1562.
Arai, T., et al. (2001). Effect of herb supplement on hepatic enzyme activities in ddY mice. Lab Anim. 35(3):288-291.
Chou, S. T., et al. Antimutagenic potential of *Graptopetalum paraguayense*E. Walther. 2004 Institute of Food Technologists Annual Meeting. Jul. 12-16, 2004, Session 114F, abstract 4, [retrieved Dec. 06, 2005]. Retrieved from the Internet: URL:http://ift.confex.com/ift/techprogram/paper_22911.htm, whole document.
Chung, Y. C., et al. (2005). Studies on the antioxidative activity of *Graptopetalum paraguayense* E. Walther. Food Chemistry 91:419-424.
Hsieh, C.L., et al. (2005). Inhibitory effect of some selected nutraceutic herbs on LDL glycation induced by glucose and glyoxal. J Ethnopharmacol. 102(3):357-363.
Huang, K., et al. (2005). Studies on the inhibitory effect of *Graptopetalum paraguayense* E. Walther extracts on mushroom tyrosinase. Food Chemistry 89:583-587.

(Continued)

*Primary Examiner*—Michele Flood
(74) *Attorney, Agent, or Firm*—Occhiuti, Rohlicek, & Tsao LLP (57) ABSTRACT

The present invention relates to compositions comprising *Graptopetalum* and uses thereof *Graptopetalum* can protect animals from liver diseases and medical conditions, such as inflammation, steatosis, and fibrosis. In particular, *Graptopetalum* inhibits proliferation of activated hepatic stellate cells, which play a pivotal role in liver fibrosis. *Graptopetalum* also has anti-fibrosis activities as well as inhibits proliferation of lung fibroblasts. Therefore, in addition to being a prophylactic and therapeutic agent for the liver, *Graptopetalum* is useful against fibrosis or inflammation of tissues or organs other than the liver, in particular lung, kidney, and bladder. Other plants in the family of Crassulaceae, particularly *Echeveria*, have similar effects as *Graptopetalum*.

11 Claims, 5 Drawing Sheets

OTHER PUBLICATIONS

Kang, T.H., et al. (2000). Antiproliferative effects of alkaloids from *Sedum sarmentosum* on murine and human hepatoma cell lines. J Ethnopharmacol. 70(2):177-182.

Wu, X. L., et al. (2003). Effect of compound rhodiola sachalinensis A Bor on $CCl_4$-induced liver fibrosis in rats and its probable molecular mechanisms. World J Gastroenterol. 9(7):1559-1562.

* cited by examiner

PHARMACEUTICAL USE OF GRAPTOPETALUM AND RELATED PLANTS

FIELD OF THE INVENTION

This invention relates to the therapeutic and prophylactic effects of *Graptopetalum* and related plants, particularly for liver-related diseases and medical conditions.

REFERENCES

U.S. Pat. No. 5,023,252.

Desmet, V. J., et al. (1994). Classification of chronic hepatitis: diagnosis, grading and staging. *Hepatology* 19(6): 1513-1520.

Friedman, S. L. (1993). The cellular basis of hepatic fibrosis. Mechanism and treatment strategies. *N Engl J Med.* 328(25):1828-1835.

Giladi, H., et al. (2003). Small interfering RNA inhibits hepatitis B virus replication in mice. *Mol Ther.* 8(5):769-776.

Pines, M. (1997). Halofuginone, a specific inhibitor of collagen type I synthesis, prevents dimethylnitrosamine-induced liver cirrhosis. *J Hepatol.* 27(2):391-398.

Saller, R., et al. (2001). The use of silymarin in the treatment of liver diseases. *Drugs.* 61(14):2035-2063.

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

BACKGROUND OF THE INVENTION

The liver is a multi-functional organ. Its basic functions can be divided into three categories: (1) the vascular functions for storage and filtration of blood, (2) the metabolic functions which are involved with most of the metabolic systems of the body, and (3) the secretory and excretory functions responsible for bile formation. Major activities of both the liver include detoxification and elimination of both endogenous and exogenous toxins, deamination of amino acids and formation of urea, regulation of blood sugar through the formation of glycogen, production of plasma proteins, production and secretion of bile, and phagocytosis of particulate matter from the splanchnic (intestinal) circulation.

As a result of liver's many different roles, when the liver is damaged, its various functions are disturbed simultaneously in different combinations, depending on the nature and location of the damage. Liver damage from any source may result in liver regeneration, necrosis (cell death), degeneration, inflammation, fibrosis, or combinations of these processes. Although the liver has great functional reserves, with progressive injury, disruption of liver function can have life-threatening consequences. Cirrhosis, which is a common end-stage liver disease, is one of the top ten causes of death in the Western world.

Despite the significance and potential severity of liver disease, therapeutic approaches are limited. Many types of liver disease are the result of viruses (e.g., hepatitis A, B, C, D, and E), and effective anti-viral therapies are rare and often cause potentially severe side effects. Other liver diseases are the results of previous toxic exposure (such as alcoholic cirrhosis and exposure to toxic plants, or environmental pollutants). In still other cases, liver diseases are the result of poorly understood interplay of various factors, including genetic factors, environmental conditions, and immune system activity (autoimmune hepatitis). No matter what the causes are, therapeutic approaches to liver diseases are complicated by two factors. Since the liver is responsible for detoxification, any use of drugs may increase the burden upon the liver and lead to deterioration of the condition. Furthermore, liver fibrosis, which occurs in many liver diseases and conditions, is generally an irreversible process. Consequently, the usable portion of the liver decreases with the progress of fibrosis, resulting in increasing complications of other organs that rely on liver functions.

Therefore, a pharmaceutical agent for the liver should ideally prevent fibrosis from occurring or progressing. In addition, it is also desirable if the agent does not pose a metabolic burden on the liver, as well as has few or no side effects.

SUMMARY OF THE INVENTION

The present invention provides, inter alia, compositions that comprise *Graptopetalum*. The inventors discovered that this common plant can protect animals from a toxic substance that causes inflammation and fibrosis of the liver, weight loss, spleen swelling, and ultimately death. With the administration of *Graptopetalum*, inflammation and fibrosis were significantly inhibited; body weight, liver weight, and spleen weight of the animals were nearly normal; and the survival rate was greatly improved. In particular, *Graptopetalum* inhibits proliferation of activated hepatic stellate cells, which play a pivotal role in liver fibrosis. Consistent with this observation, *Graptopetalum* inhibits the accumulation of collagen and prevents fibrosis to occur or progress. In addition, the composition, even at a high dosage, displayed no detectable side effects. *Echeveria* had similar effects.

Accordingly, one aspect of the present invention provides a pharmaceutical composition comprising *Graptopetalum* or *Echeveria*. The *Graptopetalum* may be any *Graptopetalum* species or in any form of preparation. Preferably, the *Graptopetalum* species is *Graptopetalum paraguayense*. Similarly, the *Echeveria* may be any *Echeveria* species or in any form of preparation. Preferably, the *Echeveria* species is *Echeveria peacockii*. The *Graptopetalum* or *Echeveria* is preferably an extract, particularly an extract of one or more aqueous solvents, nonpolar solvents, alcohol solvents, or mixtures thereof.

The pharmaceutical composition may further comprise a pharmaceutically acceptable excipient or carrier. The pharmaceutical composition may also comprise at least one other agent, particularly an agent that has anti-inflammatory, anti-steatosis, anti-viral, or anti-fibrosis, activities. For example, the agent may be selected from the group consisting of arbutin, lemon extract, cucumber extract, mercaptosuccinic acid, mercaptodextran, kojic acid, derivatives of kojic acid, vitamin C, hydroquinone, glutathione, cysteine, mulberry extract, licorice extract, and bearberry extract.

The pharmaceutical composition may be formulated for any suitable route of administration, preferably oral or topical administration.

Another aspect of the present invention provides a method of preventing or treating a liver disease or medical condition in a subject, comprising administering an effective amount of the pharmaceutical composition described herein to the subject, wherein the liver disease or medical condition is selected from the group consisting of liver inflammation, liver steatosis, liver fibrosis, liver cirrhosis, and hepatitis B.

When used for liver fibrosis or cirrhosis, it is preferable that the composition is capable of reducing the expression of smooth muscle α-actin, particularly in hepatic stellate cells.

Another aspect of the present invention provides a method for inhibiting hepatic stellate cell proliferation, comprising contacting hepatic stellate cells with the pharmaceutical composition comprising *Graptopetalum* or *Echeveria*. Yet another aspect of the present invention provides a method for selectively killing hepatic stellate cells, comprising contacting hepatic stellate cells with the pharmaceutical composition comprising *Graptopetalum* or *Echeveria*. The hepatic stellate cells are preferably located in a mammal, and most preferably in a human.

Also provided is a method for inhibiting hepatitis B virus surface antigen expression in a mammal, comprising administering to the mammal the pharmaceutical composition. The mammal is preferably a human.

In addition to *Graptopetalum* and *Echeveria*, other succulent plants in the family Crassulaceae can also be used in the same manner as described herein. This family includes the genera *Adromischus, Aeonium, Aichryson, Bryophyllum, Chiastophyllum, Cotyledon, Crassula, Cremnophila, Diamorpha, Dudleya, Echeveria, Graptopetalum, Greenovia, Hylotelephium, Hypagophytum, Jovibarba, Kalanchoe, Kitchingia, Lenophyllum, Meterostachys, Monanthes, Orostachys, Pachyphytum, Perrierosedum, Pistorinia, Prometheum, Pseudosedum, Rhodiola, Rosularia, Sedella, Sedum, Sempervivum, Sinocrassula, Tacitus, Telmissa, Thompsonella, Tylecodon, Umbilicus,* and *Villadia. Graptopetalum* and *Echeveria* are the preferred genera for the practice of the present invention.

Other aspects of the present invention provides methods for treating or preventing fibrosis or inflammation of other tissues and organs, such as the lung, kidney, and bladder, by using *Graptopetalum* or its related plants.

DETAILED DESCRIPTION OF THE INVENTION

The present invention is directed to compositions comprising *Graptopetalum* and/or related plants, and uses thereof. *Graptopetalum* can protect animals from a toxic substance that causes inflammation and fibrosis of the liver, weight loss, spleen swelling, and ultimately death. In particular, *Graptopetalum* inhibits proliferation of activated hepatic stellate cells, which play a pivotal role in liver fibrosis. The anti-fibrosis activities of *Graptopetalum* are not limited to the liver. *Graptopetalum* also inhibits proliferation of lung fibroblasts, and protects animals from a toxic substance that causes inflammation and fibrosis in the lung. Therefore, *Graptopetalum* is a prophylactic and therapeutic agent, particularly for tissue fibrosis. Plants related to *Graptopetalum* can be used in the same manner.

Prior to describing the invention in further detail, the terms used in this application are defined as follows unless otherwise indicated.

Definitions

"*Graptopetalum*", as used herein, refers to any plant in the genus of *Graptopetalum*, or part or parts thereof. The plant parts may include, without being limited to, leaves, flowers, stalks, roots, fruits, and seeds. This term also encompasses modified forms of the plant or part(s), such as powders, extracts, dried extracts, homogenates, granules, or precipitates. Combinations of more than one species of *Graptopetalum*, or parts thereof, are also contemplated. The *Graptopetalum* is preferably *G. paraguayense*.

"*Echeveria*", as used herein, refers to any plant in the genus of *Echeveria*, or part or parts thereof. The plant parts may include, without being limited to, leaves, flowers, stalks, roots, fruits, and seeds. This term also encompasses modified forms of the plant or part(s), such as powders, extracts, dried extracts, homogenates, granules, or precipitates. Combinations of more than one species of *Echeveria*, or parts thereof, are also contemplated. The *Echeveria* is preferably *Echeveria peacockii*.

An "extract" is a solution obtained by soaking or mixing a substance to be extracted with a solvent. Typically, an extract is prepared by drying *Graptopetalum* and subsequently cutting or grinding the dried material. The extraction process may then be performed with the help of an appropriate choice of solvent, typically water, ethanol, ethanol/water mixture, methanol, propanol, iso-propanol, butanol, iso-butanol, acetone, hexane, petroleum ether, or other organic solvents by means of, e.g., maceration, percolation, repercolation, counter-current extraction, turbo-extraction, or carbon-dioxide hypercritical (temperature/pressure) extraction. The extract may then be further evaporated and thus concentrated to yield a soft extract (extractum spissum) and/or eventually a dried extract, extracum siccum, by means of, e.g., spray drying, vacuum drying, fluid-bed drying, or freeze-drying. Preferably, the extract is prepared without boiling *Graptopetalum* or its related plant. It is also preferable that no oil is used to extract the plants.

"Preventing" a disease or medical condition means preventing the symptoms of the disease or medical condition from manifestation prior to onset of the disease or medical condition.

"Treating" a disease or medical condition means the reduction or complete removal of the symptoms of the disease or medical condition after onset of the disease or medical condition.

A "liver disease or medical condition" is a disease or medical condition involved with damages of the liver, or any part thereof. Liver diseases and medical conditions include, without being limited to, liver fibrosis, liver cirrhosis, chronic hepatitis (such as A, B, C, D, E, or other forms), non-alcoholic fatty liver, alcoholic fatty liver, and liver tumors (particularly hepatic carcinoma).

An "effective amount" is an amount of an agent sufficient to achieve the intended purpose. For example, an effective amount of *Graptopetalum* to treat liver cirrhosis is an amount sufficient to reduce or remove the symptoms of liver cirrhosis, as compared to the symptoms manifest in the absence of *Graptopetalum*. The effective amount of a given agent will vary with factors such as the nature of the agent, the route of administration, the size and species of the animal to receive the agent, and the purpose of the administration. The effective amount in each individual case may be determined empirically by a skilled artisan according to the disclosure herein and established methods in the art.

The term "unit dosage forms" refers to physically discrete units suitable as unitary dosages for human subjects and other mammals, each unit containing a predetermined quantity of *Graptopetalum* calculated to produce the desired effect, in association with a suitable pharmaceutical excipient.

Effects of *Graptopetalum* on Fibrosis and Inflammation

*Graptopetalum* is a succulent plant with leaves arranged in the shape of rosettes. The genus *Graptopetalum* contains 12 species, including *G. paraguayense* (Ghost Plant), *G. amethystinum* (Lavender Pebbles), *G. bellum* (also known as *Tacitus bellus*), and *G. macdougallii*.

In order to examine the effects of *Graptopetalum* on damaged liver, we utilized an animal model of liver injuries. Thus, rats were injected with a toxic chemical, dimethylnitrosamine (DMN), which caused inflammation and fibrosis of the liver. Liver functions were lower in these animals, as indicated by a variety of biochemical parameters. Body weight and liver weight both declined, while spleen weight increased, and the majority of these animals died within weeks. In contrast, the rats that received *Graptopetalum* in addition to DMN had nearly normal body and liver weights, and their spleens did not swell (Example 1). The majority of these animals survived, and their liver function indicators, including the glutamic oxaloacetic transaminase (GOT), glutamic pyruvic transaminase (GPT), prothrombin time (PT), platelet, bilirubin and albumin levels, were relatively normal (Example 2). Therefore, *Graptopetalum* dramatically reduced the damaging effects of DMN on the liver. A known therapeutic agent for the liver, silymarin (Saller et al., 2001), was examined in parallel as a positive control. Silymarin was also capable of increasing animal survival, body and liver weight, as well as liver functions. *Graptopetalum*, however, was even more effective than silymarin.

DMN is known to cause liver inflammation and fibrosis. Indeed, after DMN treatment for three weeks, the liver showed massive necrosis and infiltration of inflammatory cells upon a histochemical analysis (Example 3). The rats that also received *Graptopetalum*, on the other hand, had little or no necrosis or infiltration, indicating that *Graptopetalum* can be used to treat or prevent inflammation.

The effects of *Graptopetalum* on liver fibrosis were also examined. After DMN treatment, a fine, uniform granulation was observed on the surface of the liver. Microscopic analysis revealed cirrhotic-like structural patterns in the liver: fibrous connective tissue components in Glisson's sheath, pseudolobule formation, formation of fibrotic septa, and thickened reticulin fibers joining the central areas. Animals treated with both DMN and silymarin still exhibited intense centrilobular and periportal deposition of fibrous connective tissues. In contrast, the livers of DMN-treated rats that received *Graptopetalum* showed only mild bridging fibrosis, diminished fibrosis in both the periportal and centrilobular areas, and reduced deformation of the liver acinus (Example 4).

In a fibrotic liver, extracellular matrix accumulates. The increased levels of extracellular matrix are crucial for further progression of fibrosis, which ultimately leads to liver cirrhosis. Since collagen is a main component in the extracellular matrix, we determined the collagen content of animals treated with DMN alone or the combination of DMN and *Graptopetalum*. Although there were very low levels of collagen deposition in the livers of control rats, DMN-treated rats displayed bundles of collagen surrounding the lobules and large fibrous septa, indicating the onset of severe fibrosis. Quantitative analysis of fibrosis revealed that the *Graptopetalum* and silymarin treatments significantly reduced the DMN-induced hepatic collagen content, by 80% and 25%, respectively (Example 5).

Specific liver cells, the hepatic stellate cells (HSC), are responsible for the increase in extracellular matrix in the fibrotic liver. In normal livers, HSCs, which are lipocytes in nature, are the primary storage depot for retinoids. These cells can be identified by prominent intracellular droplets that contain vitamin A. Upon activation, HSCs undergo cell proliferation and increased fibrogenesis to result in fibrosis (see, e.g., Friedman, 1993). Since activated HSCs, as opposed to resting HSCs, produce large amounts of smooth muscle α-actin (α-SMA) mRNA and protein, α-SMA is marker of activated HSC and liver fibrosis. As expected, intense, specific staining for α-SMA was observed in the pericentral area of the DMN-treated livers. This DMN-induced expression of α-SMA was suppressed dramatically by oral administration of *Graptopetalum* or silymarin, while *Graptopetalum* was more effective than silymarin (Example 6). Taken together, these results thus indicate that *Graptopetalum* can reduce or prevent liver fibrosis, perhaps through its effects on HSCs.

We incubated cultured HSCs with *Graptopetalum* to determine the possible mechanism of *Graptopetalum* action on HSCs. The results show that *Graptopetalum* inhibited HSC proliferation in a time- and dosage-dependent manner. After a few days of incubation, the HSC changed in morphology, detached from the culture container, and died (Example 7). In contrast, hepatocytes, which were incubated in the same fashion, were not significantly affected. Thus, *Graptopetalum* is selectively cytotoxic to HSC.

Accordingly, the present invention provides a method of treating or preventing liver fibrosis or cirrhosis in a subject by administering an effective amount of *Graptopetalum* to the subject. The amount of *Graptopetalum* is preferably sufficient to reduce collagen formation, to inhibit HSC proliferation, and/or to inhibit α-SMA mRNA or protein expression, in the liver of the subject. The subject may begin to receive *Graptopetalum* before any sign of liver fibrosis is manifest; alternatively, the subject may receive *Graptopetalum* after liver fibrosis, or even cirrhosis, has begun. Almost all chronic liver conditions eventually cause liver cirrhosis. Therefore, *Graptopetalum* can be used to ameliorate the symptoms of a variety of liver diseases or conditions, including chronic hepatitis (such as A, B, C, D, E, or other forms), non-alcoholic fatty liver, alcoholic fatty liver, and liver tumors (particularly hepatic carcinoma).

Another aspect of the present invention provides a method of inhibiting HSC proliferation by using *Graptopetalum*. HSC proliferation may be measured by counting HSC numbers, determining biochemical markers of HSC (such as α-SMA mRNA or protein expression), determining collagen levels, or any other methods established in the art.

Another aspect of the present invention provides a method for preventing or treating inflammation in the liver of a subject, comprising administering an effective amount of *Graptopetalum* to the subject. It is contemplated that *Graptopetalum* can be used alone or in conjunction with other anti-inflammatory agents. These other anti-inflammatory agents may include, without being limited to, glucocorticoids, aspirin, ibuprofen, cyclopentenone prostaglandins, sesquiterpene lactones, sulfasalazine, chlorpheniramine maleate, clemastine, and deoxyspergualin. When *Graptopetalum* is administered in combination with at least one other anti-inflammatory agent, *Graptopetalum* and the other agent may be mixed in one composition for administration to the subject, or they can be administered separately.

We further discovered that *Graptopetalum* can inhibit the expression of hepatitis B virus surface antigen (Example 8). Since interference with the expression of the hepatitis B virus surface antigen has been shown to inhibit hepatitis B virus replication (see, e.g., Giladi et al., 2003), *Graptopetalum* can be used to inhibit replication of the virus as well. The present invention thus provides a method for treating or preventing hepatitis B virus infection in a subject, comprising administering to the subject an effective amount of *Graptopetalum*. *Graptopetalum* can be used alone or in conjunction with other anti-viral agents. These other anti-viral agents may include, without being limited to, interferon, lamivudine (3TC), adefovir, ribavirin, specific antibodies for the virus of interest, and combinations thereof. When *Graptopetalum* is administered in combination with at least one other anti-viral agent, *Graptopetalum* and the other agent may be mixed in one composition for administration to the subject, or they can be administered separately.

It is contemplated that *Graptopetalum* can also be used to treat or prevent fibrosis of other tissues or organs, such as the lung, kidney, bladder, or the like. Thus, administration of *Graptopetalum*, such as by the methods described herein, can reduce or prevent abnormal accumulation of extracellular matrix material in a tissue. Similarly, *Graptopetalum* can be used to treat or prevent inflammation in tissues or organs other than the liver as well. Examples 10 and 11 demonstrate the inhibitory effects of *Graptopetalum* on lung fibroblast proliferation and lung fibrosis/inflammation.

The subject that receives *Graptopetalum* according to the present invention is preferably a mammal, more preferably a mammal selected from the group consisting of human, non-human primate, feline, canine, murine, rodent, equine, porcine, bovine and ovine, and most preferably a human. Preferably, the subject either suffers from a liver disease or medical condition, or is at risk for a liver disease or medical condition. A subject is at risk for a liver disease or medical condition if, for example, the subject consumes an above-normal level of alcohol frequently, has a family history of chronic liver diseases or conditions, expects to need blood transfusions, or is easily exposed to any hepatitis virus or hazardous material.

*Graptopetalum* does not have detectable side effects. As shown in Example 7, even long term exposure to high doses of *Graptopetalum* did not impose any significant damage to experimental animals. Therefore, it is of particular interest for a subject to use *Graptopetalum* as a health/nutrition food on a regular basis. Thus, *Graptopetalum* can be mixed in food or feed, made into a drink, taken in the form of tablets, capsules, pills, powders, or the like. For the ease of regular consumption, packets comprising *Graptopetalum* powders can be prepared that can be easily made into a drink. Cookies, crackers, cakes, chips, or other snacks that contain *Graptopetalum* are also contemplated. In general, the recommended daily dosage of *Graptopetalum* is the equivalent of from 0.1 grams to 30 grams of the *Graptopetalum* whole plant (wet weight) per kilogram body weight. The dosage is preferably 0.3 to 20, more preferably 0.5 to 15, and yet more preferably 1 to 10 (grams per kilogram body weight).

Although the preferred route of administration is oral, *Graptopetalum* can be administered in any other manner. For example, *Graptopetalum* can be administered subcutaneously, intravascularly, intravenously, intraperitoneally, topically, nasally, or pulmonarily.

We further discovered that *Echeveria*, a plant related to *Graptopetalum*, had effects similar to those described herein. *Echeveria* and *Graptopetalum* are both genera in the family of Crassulaceae. This is a family of succulent, tender and cold-hardy plants, including the genera *Adromischus, Aeonium, Aichryson, Bryophyllum, Chiastophyllum, Cotyledon, Crassula, Cremnophila, Diamorpha, Dudleya, Echeveria, Graptopetalum, Greenovia, Hylotelephium, Hypagophytum, Jovibarba, Kalanchoe, Kitchingia, Lenophyllum, Meterostachys, Monanthes, Orostachys, Pachyphytum, Perrierosedum, Pistorinia, Prometheum, Pseudosedum, Rhodiola, Rosularia, Sedella, Sedum, Sempervivum, Sinocrassula, Tacitus, Telmissa, Thompsonella, Tylecodon, Umbilicus,* and *Villadia*. It is contemplated that other succulent plants from the Crassulaceae family can be used in lieu of, or in combination of, *Graptopetalum* and/or *Echeveria*. For example, the prophylactic or therapeutic composition of this invention may comprise *Graptopetalum* and optionally one or more plants from the Crassulaceae family, preferably *Echeveria*, more preferably *Echeveria peacockii*.

Compositions

This invention also includes pharmaceutical compositions which contain, as the active ingredient, *Graptopetalum*, as well as pharmaceutically acceptable carriers or excipients. As discussed above, other succulent plants from the Crassulaceae family can be used in lieu of, or in combination of, *Graptopetalum*. Therefore, although the preparation and use of compositions comprising *Graptopetalum* are discussed below, it is contemplated that other succulent plants from the Crassulaceae family are useful in the same manner.

In making the compositions of this invention, the *Graptopetalum* is usually mixed with an excipient, diluted by an excipient, or enclosed within such a carrier which can be in the form of a capsule, sachet, paper, or other container. When the pharmaceutically acceptable excipient serves as a diluent, it can be a solid, semi-solid, or liquid material, which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills, and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, acetyl alcohol, and cellulose acetate.

The liquid forms in which the compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device, or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of *Graptopetalum* in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on-demand delivery of pharmaceutical agents.

Other suitable formulations for use in the present invention can be found in Remington's Pharmaceutical Sciences.

The pharmaceutical composition may be provided in convenient kits wherein the necessary materials are packaged into suitable containers. The compositions can be administered in a single dose, or multiple doses (i.e., more than one dose). The multiple doses can be administered concurrently, or consecutively (e.g., over a period of days or weeks). The compositions are preferably formulated in a unit dosage form, each dosage containing the equivalent amount of from about 1 to 500 grams of the whole *Graptopetalum* plant (wet weight).

It is further contemplated that the compositions of the present invention may be administered in conjunction with a known anti-inflammatory agent, anti-steatosis agent, anti-viral, or anti-fibrosis agent. In addition, other substances commonly used to protect the liver, such as silymarin, can also be used in conjunction with the *Graptopetalum* composition. All of these agents or substances can be mixed in the same composition as *Graptopetalum* or administered separately.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

° C.=degree Celsius
hr=hour
68 min minute
sec=second
µM=micromolar
mM=millimolar
M=molar
L or l=liter
ml=milliliter
µl=microliter
G or g=gram
mg=milligram
µg=microgram
DMEM=Dulbecco's modified Eagle's medium
EGF=epidermal growth factor
FBS=fetal bovine serum
MEM=modified Eagle's medium
PBS=phosphate buffered saline
PDGF=platelet derived growth factor
PEO=polyethyene oxide Materials and Methods Reagents DMN and silymarin were obtained from Sigma Company (St. Louis, Mo.). Anti-α-SMA and anti-type I collagen antibodies were purchased from Calbiochem-Merck (Cambridge, Mass.). Fast Green was purchased from Curr, BDH Chemical (Canada), and hematoxylin/eosin staining reagents were obtained from Sigma Company (St. Louis, Mo.). Kits of GOT, GPT, bilirubin, and albumin were obtained from Wako (Tokyo, Japan). The organic solvents were purchased from Sigma Chemical Co. (St. Louis, Mo.). Whatman No. 1 filter paper was bought from Fisher Scientific (Fair Lawn, N.Y.).

Preparation of *Graptopetalum*

*Graptopetalum* was purchased from a local herb farm in Taiwan. *Graptopetalum* was washed with distilled water and air dried overnight, then freeze dried at −50° C. with a freeze dryer. *Graptopetalum* was then ground to powder (100 mesh), lyophilized, and stored under sealing condition at 4°

C. until use. Unless indicated otherwise, *Graptopetalum* extract was prepared by dissolving *Graptopetalum* powder in water and gradually adding ethanol to a final concentration of 80%. After centrifugation at 1400×g for 20 min, the supernatant was filtered through a 0.22-μm filter and evaporated to dryness in a rotary evaporator. The recovery of *Graptopetalum* extract after ethanol treatment was 65% (w/w). The dried extract was dissolved in water to a concentration of 50 mg/ml as a stock solution. The stock solution was then diluted to the appropriate working solution.

Animals

Male Sprague-Dawley rats, weighing 300 to 350 g, were purchased from the National Laboratory Animal Breeding and Research Center, National Science Council, Taiwan. All experiments were performed in compliance with The National Laboratory Animal Breeding and Research Center's guidelines.

Preparation of Rats as an Animal Model for Liver Injury and Fibrosis

Liver injury and fibrosis model rats were prepared by administration of DMN as previously reported (Pines et. al., 1997) with minor modification. Briefly, DMN was diluted with phosphate-buffered saline (PBS) and injected intraperitoneally (i.p.) into rats on the first three days of each week, at seven mg/ml per day, for three weeks. The control group received injection of PBS alone.

Administration of *Graptopetalum* or Silymarin

Seventy-two rats were divided randomly into four experimental groups (n=18 in each group) as follows:
(1) PBS-water (injection of PBS i.p. and oral administration of water);
(2) DMN-water (injection of DMN i.p. and oral administration of water);
(3) DMN-*Graptopetalum* (injection of DMN i.p. and oral administration of *Graptopetalum* one week after the first DMN injection); and
(4) DMN-Silymarin (injection of DMN i.p. and oral administration of silymarin one week after the first DMN injection).

*Graptopetalum* powder or silymarin was dissolved in water and given orally once per day at a dosage of 1 g/kg body weight (*Graptopetalum* powder) or 0.4 g/kg body weight (silymarin) for five weeks starting from seven days after the first injection of DMN. Control animals received the same volume of distilled water alone. After the six-week treatment, the rats were weighed and sacrificed, blood samples were collected for determination of biochemical indicators (including GOT, GPT, bilirubin, albumin, prothrombin time, and platelet number), and livers and spleens were excised, weighed, and fixed in formaldehyde for histochemistry.

Histopathological Examination of the Liver

Liver specimens were fixed with phosphate-buffered formaldehyde, embedded in paraffin, and stained with hematoxylin-eosin. Differential staining of collagenous and non-collagenous proteins was performed with 0.1% Sirius red and 0.1% fast green as a counter staining in saturated picric acid. By this procedure collagen is stained red. The extent of fibrosis and architectural alteration was scored with a semi-quantitative method by an independent pathologist in a blind fashion using liver preparation from each group as described previously (Desmet et al., 1994). Liver tissue sections were photographed using a microscope (Olympus IX70, Japan).

Example 1

*Graptopetalum* Prevents Body and Liver Weight Loss Induced by DMN

To determine the effects of *Graptopetalum* on liver injury and fibrosis, an animal model was established using DMN, a known toxic substance to the liver. Animals which received DMN, as described in Materials and Methods, were then given *Graptopetalum* and the effects determined. The effects of *Graptopetalum* were also compared to those of silymarin, which has known hepatoprotective activities. Normal animals, which did not receive DMN, were used as controls.

The effects of oral administration of *Graptopetalum* on body and liver weights of rats with and without i.p. injection of DMN are shown in Table 1. Treatment with DMN caused a significant decrease in rat body and liver weights (DMN-water group) compared with control rats (PBS-water group). Orally fed *Graptopetalum* markedly prevented this DMN-mediated rat body and liver weight loss (DMN-*Graptopetalum* group); *Graptopetalum* also reduced DMN-mediated rat spleen weight increase. No changes in body, liver, or spleen weight were observed in normal control rats. These results indicate that *Graptopetalum* significantly reduced the detrimental impacts of DMN.

TABLE 1

Body, Liver, Spleen Weight and Survival Number after 6 Weeks of Treatment

| | Survival Number | Body Weight (g) | Liver Weight (g) | Spleen Weight (g) |
|---|---|---|---|---|
| Control | 18 | 556.5 ± 11.3 (n = 18) | 24.0 ± 1.4 (n = 18) | 1.0 ± 0.0 (n = 18) |
| DMN | 5 | 439.5 ± 10.6 (n = 5) | 14.0 ± 2.8 (n = 5) | 2.0 ± 0.2 (n = 5) |
| DMN-GP | 12 | 528.5 ± 7.8 (n = 12) | 23.0 ± 1.2 (n = 12) | 1.0 ± 0.2 (n = 12) |
| DMN-Silymarin | 10 | 472.0 ± 14.1 (n = 10) | 19.5 ± 1.4 (n = 10) | 1.5 ± 0.2 (n = 10) | n, number of survived rats in the group

Figure 1:
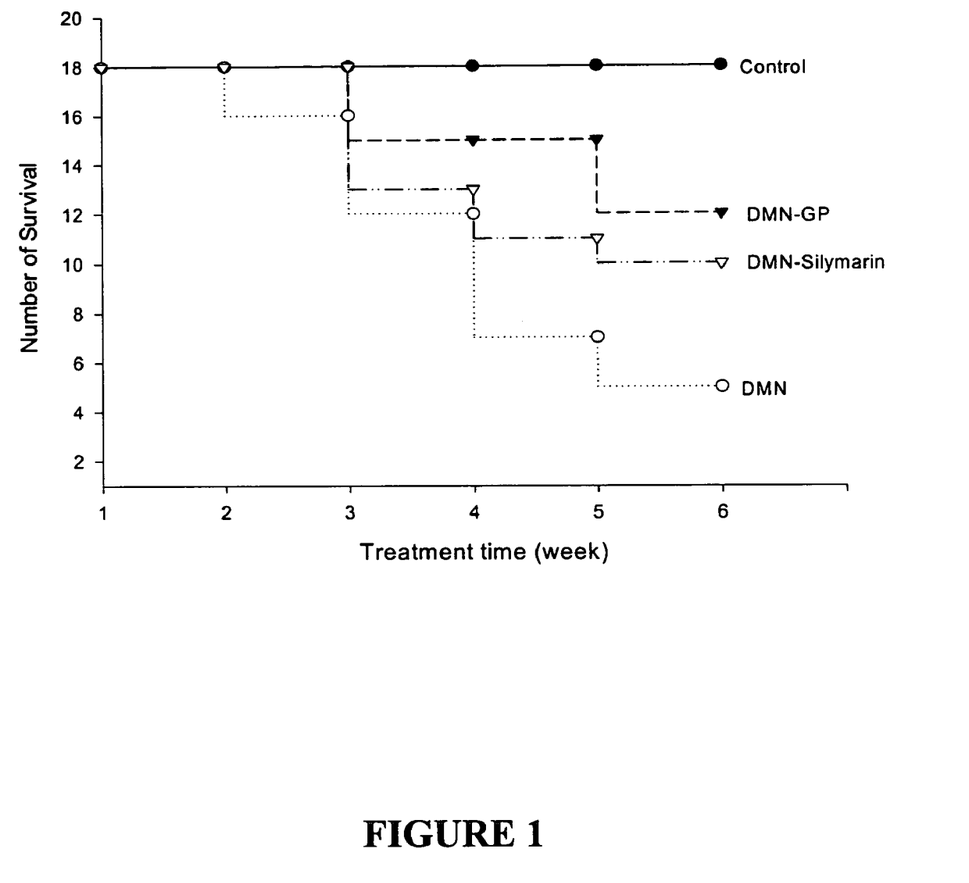
FIG. 1 shows the number of surviving rats that received vehicle control (Control), dimethylnitrosamine (DMN) and *Graptopetalum* (DMN-GP), DMN and silymarin (DMN-Silymarin), or DMN alone (DMN).

In addition, after 6 weeks, 13 out of 18 rats died in the DMN-treated group, 8 of 18 rats died in the DMN-silymarin-treated group, and only 6 of 18 rats died in the DMN-treated group orally fed with *Graptopetalum* (FIG. 1). All control rats (18 of each group) not treated with DMN, *Graptopetalum*, or silymarin survived. Therefore, *Graptopetalum* effectively protected the animals from the toxicity of DMN, and it was more effective than silymarin.

Example 2

Effects of *Graptopetalum* on Serum Bilirubin, Albumin, Platelets, and Prothrombin Time To further investigate the effects of *Graptopetalum* on liver functions, indicators of liver functions were measured. As shown in Table 2, co-administration of *Graptopetalum* prevented increases in serum GOT and GPT levels after DMN treatment. Moreover, serum bilirubin levels and prothrombin time increased in DMN-treated rats in comparison to normal controls. However, oral administration of *Graptopetalum* daily significantly prevented the bilirubin increase and albumin decrease in DMN-treated rats. In addition, treatment with DMN resulted in marked reduction of serum platelets and prolongation of prothrombin time. In contrast, improvement of prothrombin time was significant, and numbers of platelet were consistently higher in the DMN-*Graptopetalum*-treated groups.

TABLE 2

The Level of GOT, GPT, PT, PLT, Bilirubin and Albumin of Serum after 6 Weeks of Treatment

|  | GOT (U/L) | GPT (U/L) | PT (sec) | PLT ($10^3$/ul) | Bilirubin ($\mu$mole/L) | Albumin (g %) |
|---|---|---|---|---|---|---|
| Control (n = 18) | 83.0 ± 15.5 | 51.0 ± 11.3 | 12.1 ± 0.4 | 925.0 ± 49.4 | 0.13 ± 0.01 | 4.9 ± 0.3 |
| DMN (n = 5) | 651.5 ± 41.7 | 273.5 ± 13.4 | 19.8 ± 1.1 | 171.0 ± 85.5 | 1.27 ± 0.04 | 3.2 ± 0.2 |
| DMN-GP (n - 12) | 149.5 ± 2.1 | 71.0 ± 11.3 | 13.9 ± 1.4 | 818.0 ± 66.5 | 0.14 ± 0.02 | 4.9 ± 0.2 |
| DMN-Silymarin (n = 10) | 459.4 ± 37.6 | 217.5 ± 34.6 | 17.6 ± 1.2 | 334.3 ± 41.5 | 1.00 ± 0.04 | 3.5 ± 0.4 |

GOT, Glutamic Oxaloacetic Transaminase
GPT, Glutamic Pyruvic Transaminase
PT, Prothrombin Time
PLT, Platelet
n, number of survived rats in the group Accordingly, *Graptopetalum* significantly enhanced liver functions.

Example 3

Effects of *Graptopetalum* on Inflammatory and Necrosis Responses Following DMN Administration Since DMN-induced liver injury is considered to be involved in inflammatory responses, we next addressed the question whether *Graptopetalum* prevents necrosis or inflammatory responses in the liver following DMN intoxication. The results show that massive necrosis in the pericentral and mid-zonal area, with infiltration of inflammatory cells, was observed in the liver three weeks following DMN treatment. Co-administration of *Graptopetalum*, however, prevented the DMN-induced necrosis and inflammation. Thus, *Graptopetalum* can drastically prevent necrosis and inflammatory responses in the liver.

Example 4

Prevention of Hepatic Fibrogenesis by *Graptopetalum* in DMN-Treated Rats

Intraperitoneal administration of DMN resulted in a uniform fine granulation of the surface of the liver. Microscopic analysis revealed cirrhotic-like structural patterns in the liver of animals that had received DMN for six weeks: fibrous connective tissue components in Glisson's sheath, pseudolobule formation, formation of fibrotic septa, and thickened reticulin fibers joining the central areas. Animals treated with both DMN and silymarin still exhibited intense centrilobular and periportal deposition of fibrous connective tissues. In contrast, the livers of DMN-treated rats that received *Graptopetalum* for five weeks (DMN-*Graptopetalum* group) showed only mild bridging fibrosis, diminished fibrosis in both the periportal and centrilobular areas, and reduced deformation of the liver acinus. Thus, *Graptopetalum* can be used to reduce fibrogenesis of liver, which is a key development in liver cirrhosis.

Example 5

*Graptopetalum* Reduced Hepatic Collagen and Hydroxyproline Content

In a fibrotic liver, extracellular matrix accumulates. The increased levels of extracellular matrix are crucial for further progression of fibrosis, which ultimately leads to liver cirrhosis. Since collagen is a main component in the extracellular matrix, we determined the collagen content of animals treated with DMN alone or the combination of DMN and *Graptopetalum*.

The content of collagen in liver was detected by Fast Green staining. The DMN-treated rats displayed a gradual and marked increase in collagen fiber content in the liver and bundles of collagen surrounding the lobules, resulting in large fibrous septa, indicating the onset of severe fibrosis. In the DMN-silymarin-treated rats, liver collagen content was also markedly higher than that in healthy controls. However, the thickening of these collagen bundles, which stained red in the staining method used, was reduced markedly in DMN-*Graptopetalum*-treated rats. There were very low levels of collagen deposition in the livers of control rats. Quantitative analysis of fibrosis by image analysis techniques reveal that the *Graptopetalum* and silymarin treatments significantly reduced the DMN-induced hepatic collagen content by 80% and 25%, respectively.

Hepatic fibrosis was also quantified by the measurement of hepatic hydroxyproline. It was found that the hydroxyproline content of the DMN-treated group (820±31 µg/g) was significantly higher than that of the DMN-*Graptopetalum*-treated group (558±53 µg/g), DMN-silymarin-treated group (749±72 µg/g), and control group (498±22 µg/g).

Consistent with the previous two examples, these results demonstrate that *Graptopetalum* markedly prevented hepatic fibrosis.

Example 6

*Graptopetalum* Suppressed α-SMA Expression in DMN-Treated Rats

Next, the expression of α-SMA, a marker of activated HSCs, was measured. In a fibrotic liver, extracellular matrix accumulates. The increased levels of extracellular matrix are crucial for further progression of fibrosis, which ultimately leads to liver cirrhosis. Specific liver cells, the hepatic stellate cells (HSC), are responsible for the increase in extracellular matrix. Since activated HSCs, as opposed to resting HSCs, produce large amounts of smooth muscle α-actin (α-SMA) mRNA and protein, α-SMA is an indicator of activated HSC and liver fibrosis.

α-SMA was measured by immunohistochemical staining in the liver six weeks after the first DMN administration. As expected, intense, specific staining for α-SMA was observed in the pericentral area of the DMN-treated livers. This DMN-induced expression of α-SMA was suppressed dramatically by oral administration of *Graptopetalum* or silymarin, while *Graptopetalum* was more effective than silymarin. Livers from rats that received vehicle controls showed negative staining for α-SMA, as expected. Again, these findings indicate that *Graptopetalum* prevented fibrogenic responses in the liver.

Example 7

The Anti-Proliferative Effect of *Graptopetalum* Extracts on Cultured Rat Hepatic Stellate Cells Various *Graptopetalum* extracts were prepared to determine the activity of *Graptopetalum* on hepatic stellate cell. The extracts were prepared as follows:

Crude Aqueous Extract

Whole plants of *Graptopetalum* were lyophilized and powdered. Five grams of the powdered material were extracted twice with 250 mL of water at 25° C. for 2 hours on a rotary shaker at 100 rpm. The extract was pink in color after lyophilization.

Water-Ethanol Extract

The crude aqueous extract described above was stirred with activated charcoal (0.036 g/mL extracts) for 30 min. The mixture was then filtered with Whatman No. 1 filter paper, washed twice with distilled water, and extracted with 0.6 L 50% EtOH. After filtration and vacuum evaporation, 300 mg of dried ethanol extract was obtained as a dark brown paste. The main constituents were glycosides, oligomeric gallotannins, and flavonoids. Terpenoids and saponin were also detected. The dark brown paste was soluble in water and partially soluble in methanol. Precipitates from methanol were analyzed, and they contained polysaccharides and glycoproteins.

Ethanol Extract

The activated charcoal described above, after being extracted with 50% ethanol, was then extracted with 0.6 L 95% ethanol. After filtration and vacuum evaporation, 200 mg of dried ethanol extract was obtained. The main constituents of this dark brown paste were flavonoids and terpenoids.

Acetone Extract

The activated charcoal described in the last paragraph, after being extracted with 95% ethanol, was extracted with 0.6 L acetonitrile, followed by 0.6 L 70% acetone. The extracts were combined, filtered and vacuum evaporated to yield 50 mg of dried acetone extract. The main constituents were oligomeric gallotannins, flavonoids, saponin, and triterpenoids. This dark brown paste was soluble in water, ethanol, and methanol.

Chloroform Extract

The activated charcoal, after being extracted with acetone as described in the last paragraph, was extracted with 0.6 L chloroform. After filtration and vacuum evaporation, dried acetone extract was obtained as a dark brown paste. The main constituents were flavonoids, saponin, and triterpenoids. The dark brown paste was insoluble in water and partially soluble in acetone. The acetone precipitate was white in color.

Crude Methanolic Extract

Whole plants of *Graptopetalum* were lyophilized and powdered. Five grams of the powdered material were extracted twice with 250 mL of methanol at 25° C. for two hours on a rotary shaker at 100 rpm. The extract was filtered and vacuum evaporated. The resulting product was partially water soluble. The water-soluble portion contained 200 milligrams of reddish flavonoids, and the water-insoluble portion contained 400 milligrams of flavonoids and triterpens.

Figure 2:
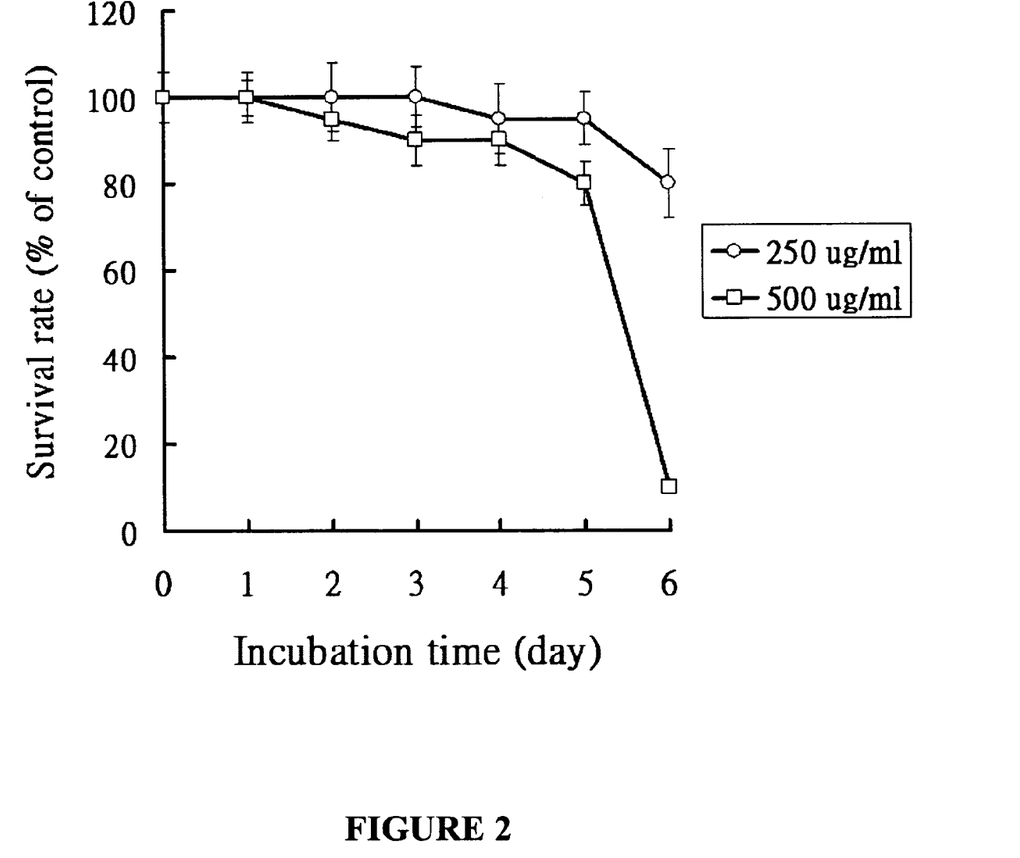
FIG. 2 shows the anti-proliferative effect of crude *Graptopetalum* extracts on cultured rat hepatic stellate cells. Rat hepatic stellate cells were incubated in 250 or 500 µg/ml of *Graptopetalum* crude extract, and the number of surviving cells was counted everyday. The survival rate shown is the percent survival rate as compared to the control cells which did not receive *Graptopetalum*.

The effects of *Graptopetalum* fractions on the proliferation of HSC was examined. The number of cells increased from $1.2\pm0.3\times10^5$ (n=9) to $3.6\pm0.5\times10^5$ (n=9) cells per well during the six-day period of culture. *Graptopetalum* extract inhibited the cell growth of HSC in a dose- and time-dependent manner. The addition of high dose *Graptopetalum* crude extract (500 µg/ml) to cultured activated rat HSCs and hepatocytes resulted in striking morphologic alterations in HSCs after five days as judged by light microscopy. Thus, HSCs changed from a flattened fibroblastic phenotype with distinct cell-cell interfaces to a substratum-detached, rounded morphology, leaving a striking extracellular matrix net structure on the bottom of the culture flasks. In contrast, the crude extract of *Graptopetalum* had almost no effect on hepatocytes at the same dose. Therefore, *Graptopetalum* was preferentially toxic to HSCs and ultimately resulted in cell death (FIG. 2). Without wishing to be limited to a theory, this selective cytotoxic effect may be the basis of the anti-fibrotic activities of *Graptopetalum*.

Figure 3:
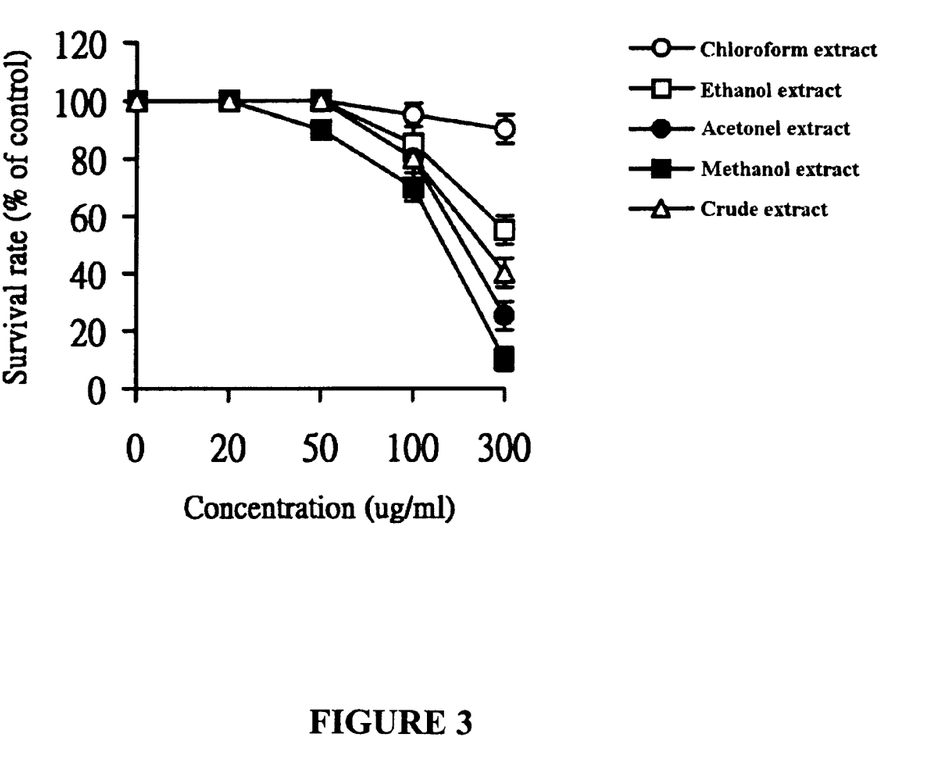
FIG. 3 shows the anti-proliferative effect of various *Graptopetalum* extracts on cultured rat hepatic stellate cells. Rat hepatic stellate cells were incubated in the indicated *Graptopetalum* extract, and the number of surviving cells was counted everyday. The survival rate shown is the percent survival rate as compared to the control cells which did not receive *Graptopetalum*.

The anti-proliferative effects of various *Graptopetalum* extracts, including the water extract, water-ethanol extract, ethanol extract, methanol extract, acetone extract, and chloroform extract as described above, were determined. As shown in FIG. 3, all the tested extracts of *Graptopetalum* exhibited cytotoxic effects on hepatic stellate cells, indicating that all these extracts have anti-fibrotic activities.

The safety of *Graptopetalum* was demonstrated by further experiments. Daily oral administration of a high dose of *Graptopetalum* (5 g/kg body weight) for 90 days did not cause any apparent adverse side effects in rats, and there was no evidence of mortality or hepatic damage upon an examination of histological sections of the liver. Moreover, these *Graptopetalum*-treated rats did not exhibit any significant change in body weight, liver weight, or serum GOT, GPT, bilirubin, and albumin levels in comparison with the control group or a low-dose *Graptopetalum*-treatment group (1 g/kg) (data not shown). Therefore, *Graptopetalum* is safe to normal cells even at a high dosage, although it effectively kills activated hepatic stellate cells.

Example 8

Inhibition of HbsAg Expression

Figure 4:
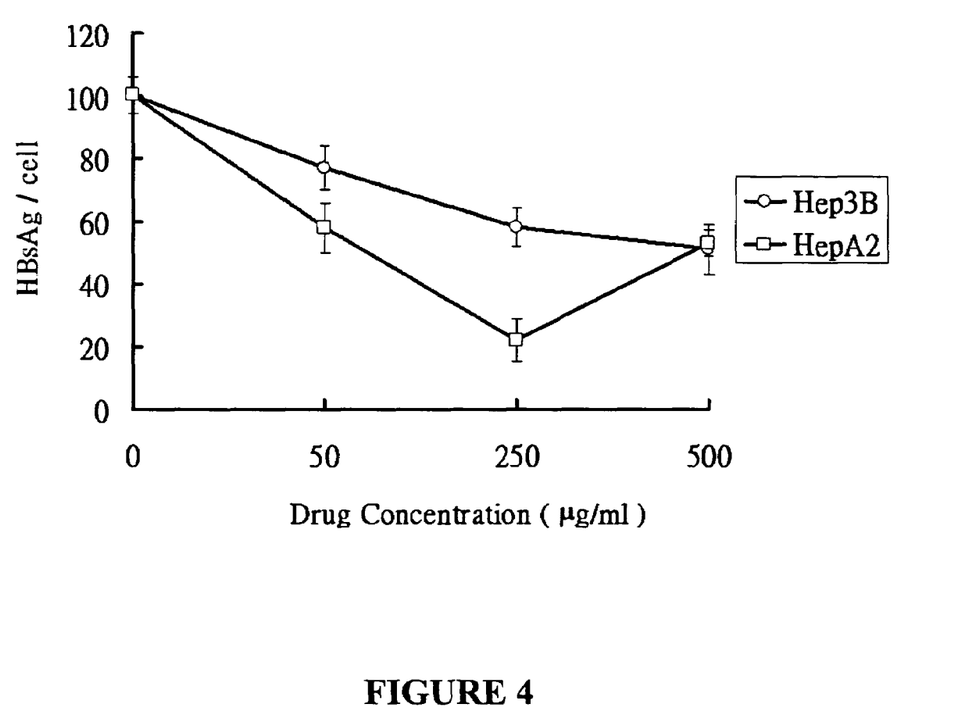
FIG. 4 shows the expression levels of HbsAg in Hep3B or HepA2 cells incubated in the indicated concentrations of *Graptopetalum* extract.

The effects of *Graptopetalum* on the hepatitis B virus was examined using human hepatoma Hep3B and HepA2 cells, which constitutively express the surface antigen of hepatitis B virus (HbsAg). After incubating Hep3B and HepA2 cells with *Graptopetalum* extracts, the expression levels of HbsAg were examined with an ELISA assay. As depicted in FIG. 4, treatment with 250 µg/ml *Graptopetalum* significantly reduced the secretion of HbsAg from Hep3B and HepA2 cells, by 75% and 40%, respectively. Therefore, *Graptopetalum* can be used to inhibit hepatitis B virus replication.

Example 9

The Effects of *Graptopetalum* on Clinical Patients

Fourteen patients were diagnosed with hepatic steatosis (10 men, 4 women; mean age 49 years). The diagnosis was confirmed by ultrasonography examination showing hepatic steatosis in all patients. The patients received an oral dose of 60-200 mg/kilogram body weight per day of *Graptopetalum* (dry powder) for six months and reexamined with ultrasonography. The results indicate that almost all patients completely recovered from hepatic steatosis. Thus, *Graptopetalum* is very effective in patients with fatty liver.

In addition, *Graptopetalum* significantly improved the biochemical markers of patients with light or moderate liver fibrosis. For example, in one study, *Graptopetalum* significantly reduced the levels of serum GOT, GPT, and bilirubin in 10 of 16 patients (11 men and 5 women; mean age 52 years) while it elevated the level of serum albumin. Based on their ultrasonography images, it was also found that *Graptopetalum* significantly reduced liver fibrosis in several patients. Moreover, *Graptopetalum* improved the quality of life for 4 patients with terminal stage of liver cirrhosis (3 men and 1 woman, mean age 51 years).

Example 10

Effects of *Graptopetalum* on Lung Fibrosis

Isolation of lung fibroblasts: Minced pieces of lung tissue was digested for 1 h with collagenase (0.5 mg/ml) and DNase (0.05 mg/ml) in Hanks' balanced salt solution which contained 0.5 mM EDTA. Cells were separated from the digested tissue by filtration through polyamide nylon mesh, collected by centrifugation, and washed once in medium. After resuspension in DMEM containing 10% FCS, cells were plated on culture plates. After three passages, cultures contained approximately 100% lung fibroblasts. Primary cultured lung fibroblasts were treated with various *Graptopetalum* extracts for five days. After the incubation, cell number was directly counted by the Trypan blue dye exclusion method.

Figure 5:
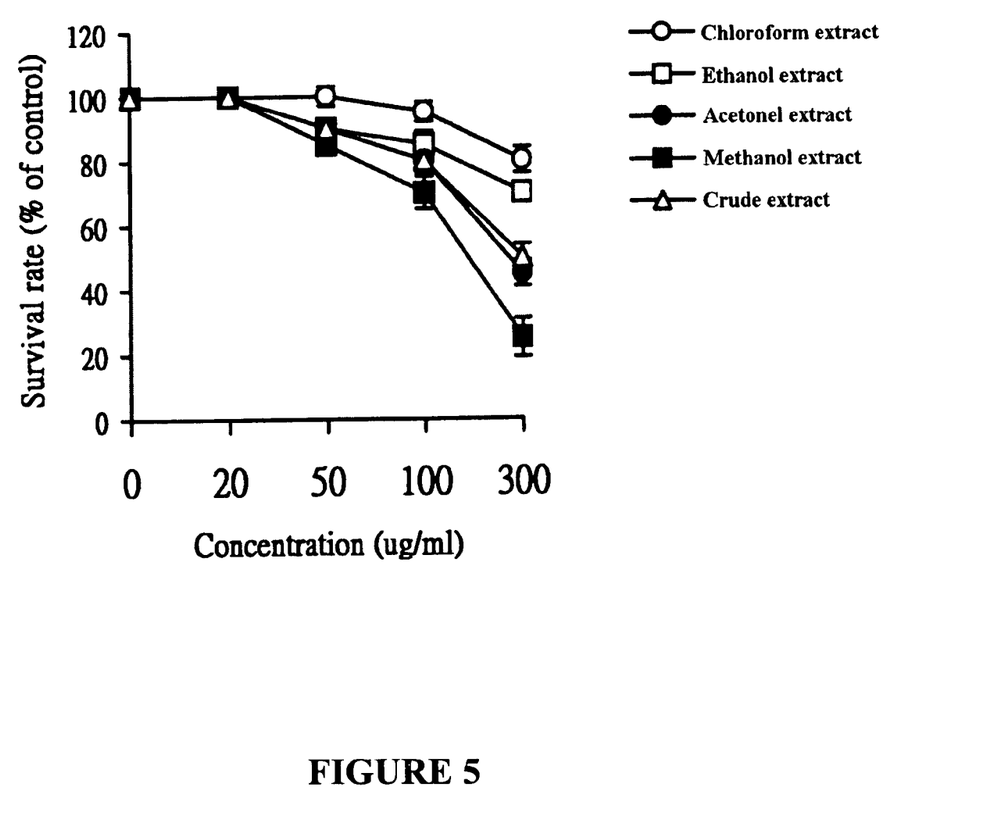
FIG. 5 shows the antiproliferative effect of various *Graptopetalum* extracts on cultured mice lung fibroblasts. Primary cultured lung fibroblasts were incubated in the indicated *Graptopetalum* extract, and the number of surviving cells was counted after incubation for five days. The survival rate shown is the percent survival rate as compared to the control cells, which did not receive *Graptopetalum* extract.

The results show that all tested *Graptopetalum* extracts inhibited cell growth of lung fibroblast in a dose-dependent manner (FIG. 5). The anti-proliferative effect on lung fibroblasts thus can serve as the basis of the anti-fibrotic activities of *Graptopetalum* in the lung.

Example 11

The Effects of *Graptopetalum* on the Lung

An animal model of bleomycin-induced pulmonary fibrosis was used to study the effect of *Graptopetalum* on the lung. Male C57BL/6 mice (6-8 weeks old) were anesthetized with ketamine and given intratracheal injections of either 0.15 U/kg of bleomycin (Blenoxane; Sigma-Aldrich, St. Louis, Mo., USA) or sterile saline. The mice were sacrificed for analysis 1, 3, 7, 14, 21 days after exposure to bleomycin. In separate experiments, mice treated with bleomycin were given daily oral administration of 1 g/kg body weight of *Graptopetalum* powder or water until sacrifice. Animal use for these studies was approved by the Institutional Animal Care and Use Committees of the Taichung Veterans General Hospital, Taiwan.

Five animals from each treatment group were randomly chosen for histologic evaluation of their lungs at the end of the experiment, as follows. After sacrifice, the lung tissue was fixed by a buffered 10% formalin solution for 48 h and embedded in paraffin. The tissues were then sectioned at 3 µm, stained with hematoxylin and eosin, and examined for inflammatory cell infiltration and pulmonary fibrosis. The criteria for scoring pulmonary fibrosis were as follows: Grade 0=normal lung; Grade 1=minimal fibrous thickening of alveolar or bronchiolar walls; Grade 2=increased fibrosis with definite damage to the lung structure and the formation of fibrous bands or small fibrous masses; and Grade 3=severe distortion of the lung structure and large fibrous areas.

All mice survived until the time of killing, but the mice treated with only bleomycin suffered significant weight loss and were in a worse condition than the mice treated with *Graptopetalum*. In the histological studies, lungs from the bleomycin/water group showed diffuse and marked infiltration of inflammatory cells, as well as increased alveolar wall thickness with typical fibrotic changes. In contrast, lungs from the bleomycin/*Graptopetalum* group showed fewer fibrotic lesions and local infiltrations of inflammatory cells. Lungs from the *Graptopetalum* group, which did not receive bleomycin, did not show any identifiable lesions, demonstrating that *Graptopetalum* itself did not cause any change to the lung. The pulmonary fibrosis scores for the bleomycin/*Graptopetalum* group (1.4±0.5) were significantly lower than that for the bleomycin/water group (2.6±0.4). The scores for the normal control group (saline/water) and the *Graptopetalum* group (saline/*Graptopetalum*) were approximately 0 and 0, respectively.

These results are consistent with those in Example 10, which indicate that *Graptopetalum* inhibits the proliferation of lung fibroblasts. Accordingly, *Graptopetalum* is effective against pulmonary fibrosis and inflammation.

A number of embodiments of the invention have been described. Nevertheless, it will be understood that various modifications may be made without departing from the spirit and scope of the invention.

I claim:

1. A method of treating a subject suffering from or susceptible to a liver disease or medical condition, comprising administering an effective amount of a pharmaceutical composition that comprises an ethanolic *Graptopetalum* extract to the subject, wherein the liver disease or medical condition is selected from the group consisting of liver inflammation, liver steatosis, liver fibrosis, liver cirrhosis, and hepatitis B.

2. The method of claim 1 wherein the ethanolic *Graptopetalum* extract is obtained from *Graptopetalum paraguayense*.

3. The method of claim 1 wherein the liver disease or medical condition is liver inflammation.

4. The method of claim 1 wherein the liver disease or medical condition is liver fibrosis.

5. The method of claim 1 wherein the liver disease or medical condition is liver cirrhosis.

6. The method of claim 1 wherein the liver disease or medical condition is hepatitis B.

7. The method of claim 1 wherein the liver disease or medical condition is liver steatosis.

8. The method of claim 1 wherein the pharmaceutical composition is administered orally.

9. A method of treating a subject suffering from or susceptible to a liver fibrosis, comprising administering to the subject an effective amount of a pharmaceutical composition that comprises a *Graptopetalum* extract.

10. The method of claim 9, wherein *Graptopetalum* extract is obtained by extracting the whole *Graptopetalum* with ethanol, acetone, chloroform, or methanol.

11. The method of claim 9, wherein the *Graptopetalum* extract is obtained from *Graptopetalum paraguayense*.

* * * * *